United States Patent [19]

Brown et al.

[11] Patent Number: 5,319,983

[45] Date of Patent: Jun. 14, 1994

[54] NOTCHING MACHINE AND METHOD FOR MECHANICAL TESTING SPECIMENS

[75] Inventors: Norman Brown, Haverford, Pa.; Alex Radin, Cherry Hill, N.J.; Xici Lu, Ardmore, Pa.

[73] Assignee: The Trustees of the University of Pennsylvania, Philadelphia, Pa.

[21] Appl. No.: 869,493

[22] Filed: Apr. 16, 1992

[51] Int. Cl.⁵ .............................................. G01N 19/08
[52] U.S. Cl. .................................................... 73/799
[58] Field of Search ................. 73/799, 834, 835, 838, 73/839

[56] References Cited

U.S. PATENT DOCUMENTS

| | | | |
|---|---|---|---|
| 2,340,401 | 2/1944 | Martin | 73/835 |
| 4,090,489 | 5/1978 | Barker | 125/13 R |
| 4,864,867 | 9/1989 | Manahan, Sr. | 73/851 |

OTHER PUBLICATIONS

Bhattacharya, S. K. et al. Micromechanisms of crack . . . polyethylene. Journal of Materials Science. vol. 19, 1984. pp. 2519-2532.

X. Lu et al., "Notchology-The Effect of the Notching Method on the Slow Crack Growth Failure in a Tough Polyethylene", *Journal of Material Science*, vol. 26, pp. 881-888 (1991).

M. K. V. Chan et al., "Slow Stable Crack Growth in High Density Polyethylenes", *Polymer*, 1983, vol. 24, Feb., pp. 234-244.

X. Lu et al., "The Correlation of Slow Crack Growth in Linear Polyethylene by the J-Integral", *Polymer*, 1989, vol. 30, Dec., pp. 2215-2221.

Japanese Product Literature of a notching device (undated).

Primary Examiner—Jerry W. Myracle
Attorney, Agent, or Firm—Synnestvedt & Lechner

[57] ABSTRACT

Notching methods and machines are provided by this invention for preparing notches in mechanical testing specimens. The notching machines razor element for creating a notch in the specimen and mechanical actuation elements for substantially linearly contacting the razor element with the specimen in a direction which is either substantially normal to the surface of the specimen receiving the notch or substantially normal to a stress created in the specimen during testing. This actuation forms a notch without any significant residual stresses forming ahead of the notch.

21 Claims, 5 Drawing Sheets

NOTCHING MACHINE AND METHOD FOR MECHANICAL TESTING SPECIMENS

FIELD OF THE INVENTION

This invention relates generally to devices and methods for preparing notches in the mechanical testing of polymer specimens, and more particularly, to procedures for preparing sharp notches in polymeric specimens which undergo slow crack growth.

BACKGROUND OF THE INVENTION

Slow crack growth is a typical failure mechanism in polymeric materials often used in industry for piping and structural applications. This mechanism in polymers is of considerable practical importance since it occurs at low stresses and can be the cause of the long-term failure in engineering components. Crack propagation is often exacerbated by environmental effects, such as corrosion and various environmental wear and stress mechanisms, which promote the growth of the crack even at lower stresses.

In many cases, cracks initiate from an inherent flaw in the material or from small defects which occur as a result of the manufacturing or installation processes. From these inherent flaws, a single macroscopic crack can propagate through the material until failure.

Recently, fracture mechanics has made it possible to monitor the behavior of a single, artificially-made sharp crack continually. This process begins by initiating a well-defined notch in a solid specimen. The intent of the notching procedure is to make a very sharp and reproducible crack initiation site.

In the case of ductile materials, such as polymer specimens, the damage introduced by the notching procedure may have a significant effect on the observed fracture and the important material parameters that determine the fracture process. The method of notching is especially important in the case of low yield point polymers, such as polyethylene, and has been studied in depth. See X. Lu, et al., "Notchology, the Effect of the Notching Method on the Slow Crack Growth Failure in a Tough Polyethylene", *Journal of Material Science*, Vol. 26, pp. 881-888 (1991), which is hereby incorporated by reference.

The Lu et al. study evaluated the effects of slow crack growth of polyethylene using a razor blade to produce a notch. The results of this study indicate that by pressing a fresh razor blade into the polyethylene specimen at a rate of 50 $\mu$m/min at room temperature, a fracture is produced at a rate which is equal to or faster than any other method previously developed. This survey also determined that other mechanical cutting procedures, such as slicing with a surgical blade, or rotary cutters, produces unacceptable residual stresses ahead of the crack, which could possibly mask the parameters of the fracture process. While the notching procedure described by Lu et al. has produced the fastest and most reproducible failure times, and has lowered the time to notch from 70 minutes to approximately 12 minutes, there is still concern in industrial applications about the time that it takes to test slow crack growth specimens.

There is, therefore, a need for a faster, more efficient, notching mechanism and testing procedure. There is also a need for a notching procedure which makes the notching step a negligible event in the overall testing of polymers and other soft materials, so as to effectively eliminate this cost factor and significant time-consuming step in the manufacturing of a wide variety of products.

SUMMARY OF THE INVENTION

This invention provides notching machines and methods for preparing a notch in a mechanical testing specimen. The machines include razor means for creating a notch in the specimen and mechanical actuation means for substantially linearly contacting the razor means with the specimen in a direction which is substantially normal to the surface of the specimen receiving the notch. This actuation is specially designed to produce a notch without any significant residual stresses forming ahead of the notch.

Accordingly, this invention provides means for producing a standard notch in a polymeric specimen in a fraction of the time normally associated with prior art procedures. Tests have been conducted which have produced notches in less than five minutes and as low as about one minute. This time would be considered negligible by most industries with respect to the failure times of the polymers and other materials now tested, and the amount of production time required to test specimens.

The notching machines of this invention are relatively inexpensive, portable, and easy to use. In further developments of this invention, notching rates are performed at a rate of less than about 3500 $\mu$m/min., and preferably about 700-1000 $\mu$m/min., at least when forming an end region of the notch. These rates achieve relatively fast times to failure without any reduction in the accuracy of the notch depth. The preferred machines function by pressing a razor blade accurately into a well-defined position on the polymer test surface. The speed is preferably set at a constant rate determined from experimental procedures designed to minimize damage produced by the razor blade so that it does not effect the fracture characteristics of the polymer, and does not generate excess time spent in notching the specimen. The testing procedures of this invention can be used for a variety of materials, including polymers, such as polyethylene and nylon, and composite products, such as graphite or glass-reinforced epoxy. Polymers which have a higher yield point than polyethylene, such as PLEXIGLASS ®, may be tested in accordance with this invention by setting the instruments to different speeds by simple modification of the gears or motor settings. Dial gauges are provided for accurately controlling the depth of the notch to within plus or minus 0.01 mm. The devices of this invention can also be equipped with alignment means located between the razor means and the specimen for maintaining a definite relative position between the specimen and razor means for use with both flat specimens and those cut from pipe.

BRIEF DESCRIPTION OF THE DRAWINGS

The accompanying drawings illustrate preferred embodiments of the invention, as well other information pertinent to the disclosure, and in which.

DETAILED DESCRIPTION OF THE INVENTION

Figure 1:
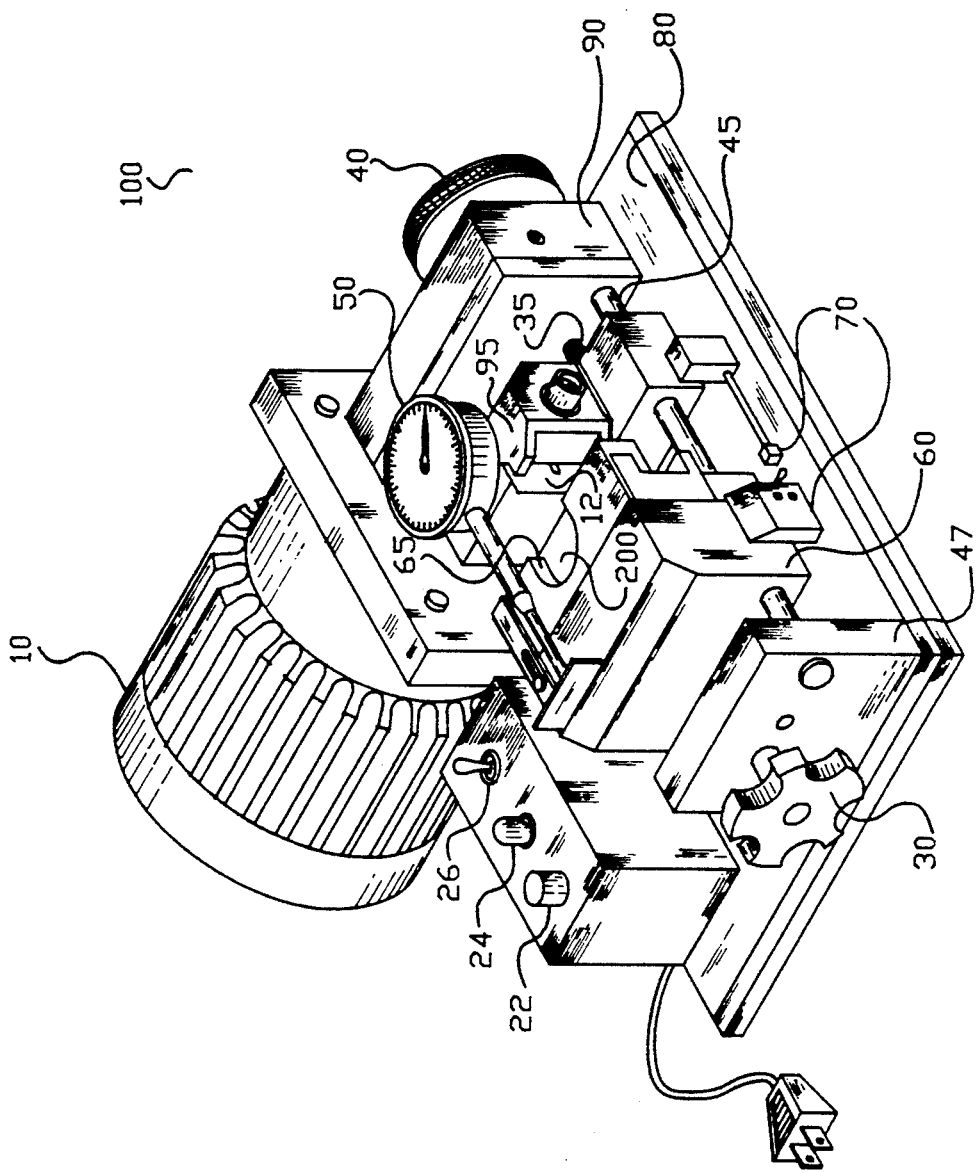
FIG. 1: is a perspective view of a preferred notching machine of this invention.
Figure 2:
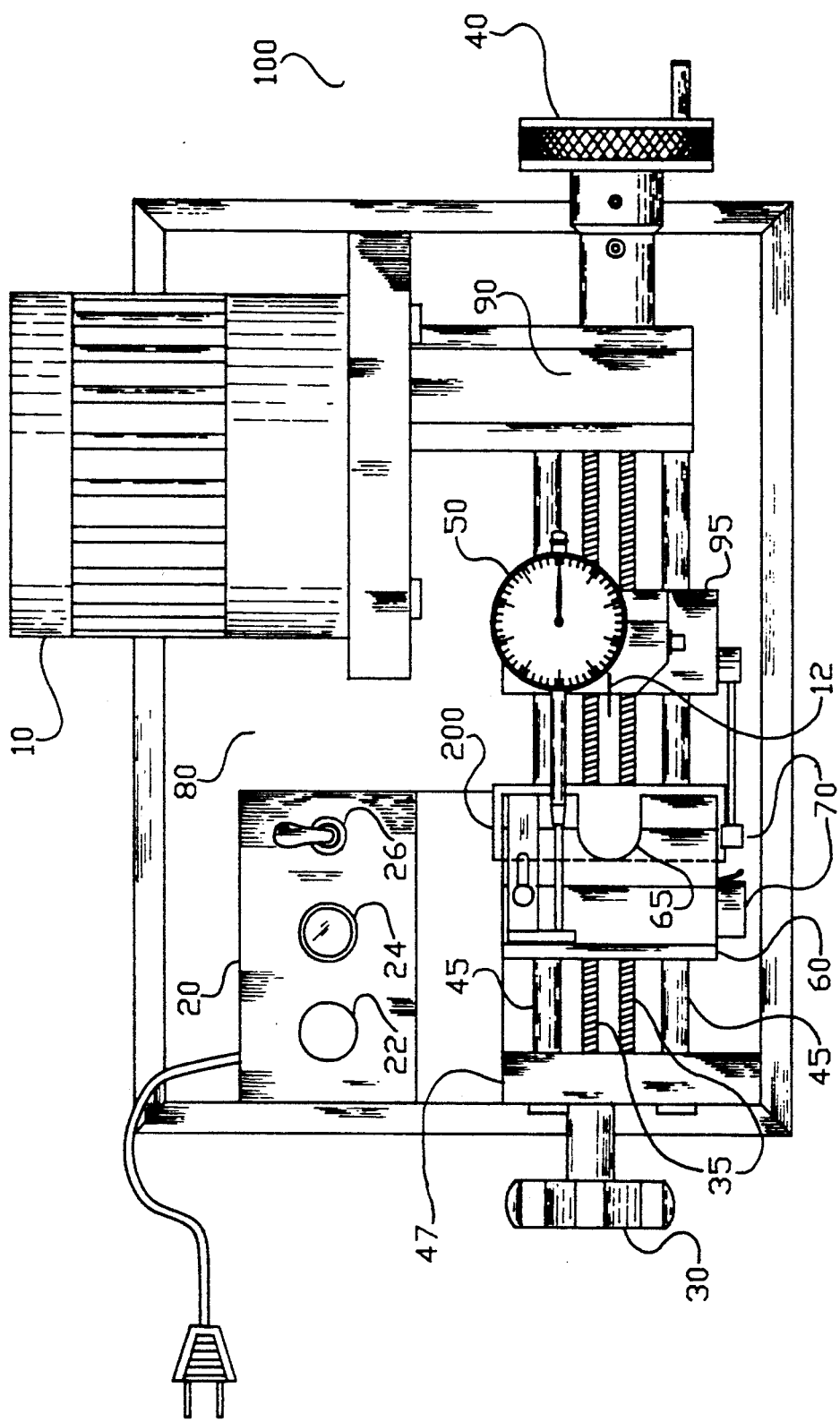
FIG. 2: is a top elevational view of the preferred notching machine of FIG. 1.

Referring to FIGS. 1 and 2 there is shown a preferred notching machine 100 used to notch the specimens tested in accordance with this invention. This machine 100 is a new design specifically created to accommodate a wide variation of notching speeds, although the machine is capable of being set for a particular speed for select applications. This machine 100 preferably includes an AC 1/12 horsepower motor 10, providing a range of machine speeds to produce a 3.5 mm standard notch depth within about 40 seconds to about 70 minutes. The motor 10 is engaged with gear box 90 for providing mechanical energy to threaded shafts 35 disposed through and engaged with holders 60 and 95. The threaded shafts 35 can be further equipped with hand adjustment knobs 30 and 40 for permitting manual linear motion, such as retraction and advancement, between the specimen holder 60 and the razor blade holder 95. The motor 10 is preferably activated with AC power source 20. This power source 20 preferably includes a fuse 22, light indicator 24, and a three-position main switch 26. The switch 26 includes both front and reverse modes, as well as a stop position.

In an important aspect of this invention, a razor means, preferably a single edge razor 12, is inserted into its holder 95. Fixed to the top portion of the razor holder 95 is a preferred metric dial indicator 50 for determining notch depth at all points during the notching procedure. The specimen 200 is inserted and clamped into specimen holder 60. The holders 60 and 95 are equipped with a limit switch system 70 for minimizing excess penetration by the razor 12 beyond the point of the predetermined notch depth, usually about 3.5 mm. The gearing mechanism is also equipped with a linear motion system including a preferred arrangement of substantially parallel rails 45, which can be, for example round or square in cross-section. These rails 45 are preferably disposed through both the specimen and razor holders at about 90° for assuring substantially linear alignment between the razor blade 12 and the specimen 200. The specimen holder 60 is designed so that it maintains a definite position relative to the razor blade 12 and can be used to secure both flat specimens and those cut from pipe or other curvilinear shapes. The specimen holder 60 can comprise a plurality of clamping members as well as a crack site window 65 for permitting razor access to the specimen without damaging the razor or changing its path.

A light source, not shown, can also be provided so that the initial placement of the razor blade 12 against the specimen 200 can be accurately accomplished in order to control the depth of the notch. The notching machine 100 can produce notch depths ranging from a few μm to up to and exceeding about 10 mm. The specimen holder 60 can be easily modified to accommodate specimens of practically any thickness.

Figure 5:
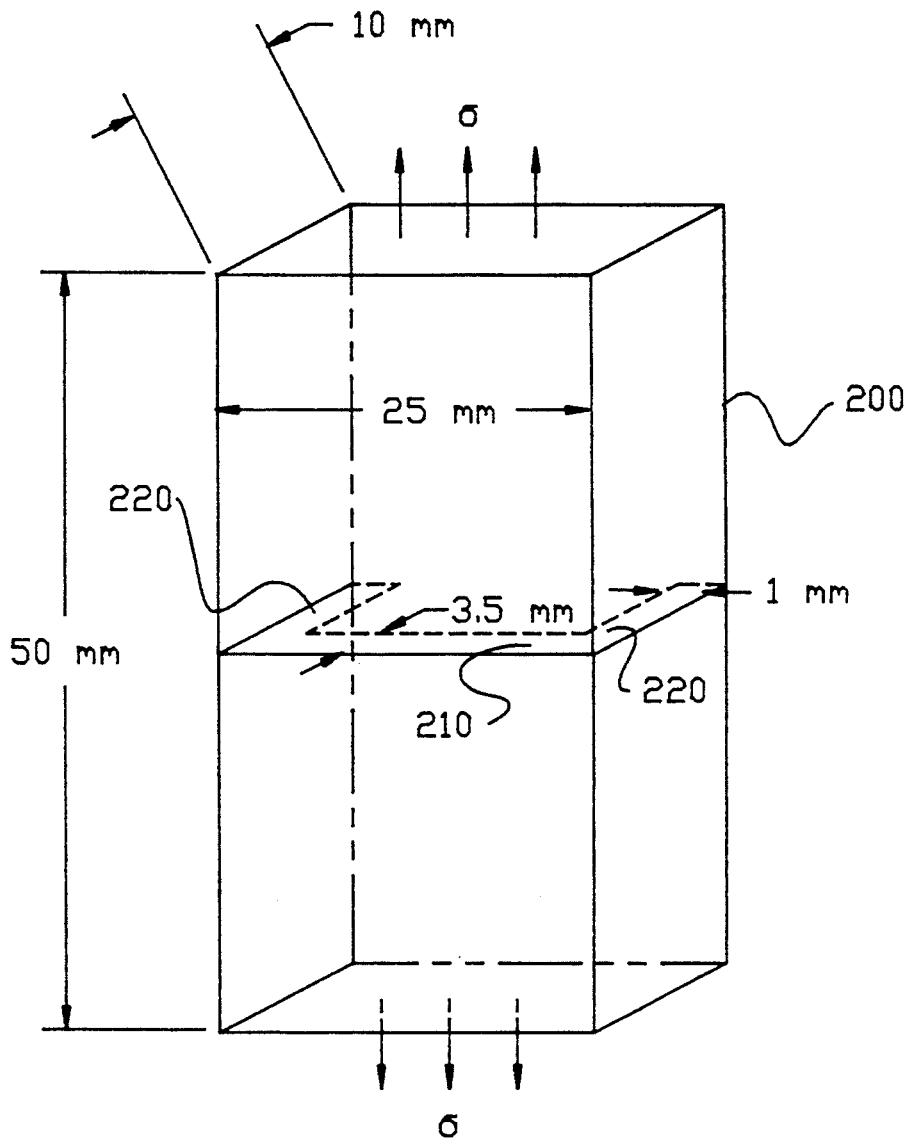
FIG. 5: is a perspective view of a preferred polymeric specimen and notch of this invention.

Referring to FIG. 5, there is shown a preferred specimen 200 indicating a stress pattern created during long-term crack growth testing. The specimen 200 includes a front notch 210 having a depth of about 3.5 mm and a pair of side notches 220 having a depth of about 1 mm each for ensuring nearly 100% plane strain. In the field of Fracture Mechanics, the side notches are called side grooves.

The notching principle of this invention were tested in a series of experiments to determine the lower limit of notching speed capable of reproducible data, the mechanism that increases failure time in crack propagation specimens at faster notching speeds, and the maximum notching speed producible without significantly increasing failure time. The resin used for this investigation was a high density polyethylene-butene polymer, XS78, manufactured by DOW Canada Inc. The molecular weight for this polymer is $M_w = 325,000$, $M_n = 35,000$, with 3 ethyl branches per 1000 c and a density of 0.952 gm/cm$^3$.

The resin was compression molded into 10 mm thick plates and then slow cooled from 180° C. to room temperature. Samples measuring 10 mm×25 mm×50 mm, shown in FIG. 5, were cut from these plates. As is standard, the notch depth for all samples was selected to be 3.5 mm with side notches of 1 mm.

The standard load of about 2.4 MPa/cm$^2$ was used to initiate a crack at the tip of the notch 210. All tests were carried out at 80° C. or less. A load of about 2.4 MPa was used as a maximum since it has been demonstrated to be the greatest load that will produce slow crack growth in polyethylene at 80° C. At temperatures much above 80° C., polyethylene samples experience significant changes in morphology. Thus, the selected combination of temperature and load parameters provided the shortest possible failure times. It is understood, however, that higher stresses could be employed at lower temperatures with similar results.

Initial testing of the samples revealed that the failure time for XS78 was approximately 400-500 minutes under the standard razor introduction speeds of about 50 μm/min. This was in agreement with the data already available for this polymer.

Further experiments showed that for speeds of approximately 350 μm/min. and 700 μm/min., there was no significant change in failure time. This information, in part, led to the presently preferred standard notching time of approximately 12 minutes for the 3.5 mm notch, or a 300 μm/min. notching speed.

Finally, a jump to a 40 second notch time for the 3.5 mm notch (notching speed = 5250 μm/min.) showed a 50% increase in failure time, up from 425 minutes to greater than 500 minutes. A summary of the averages for these data points is provided in Table I below.

TABLE I

| Average Notching Time Versus Time to Failure | |
|---|---|
| Notching Time | Failure Time |
| 13.92 min. | 436.6 min. |
| 5.46 min. | 402.5 min. |
| 0.59 min. | 677.3 min. |

Figure 3:
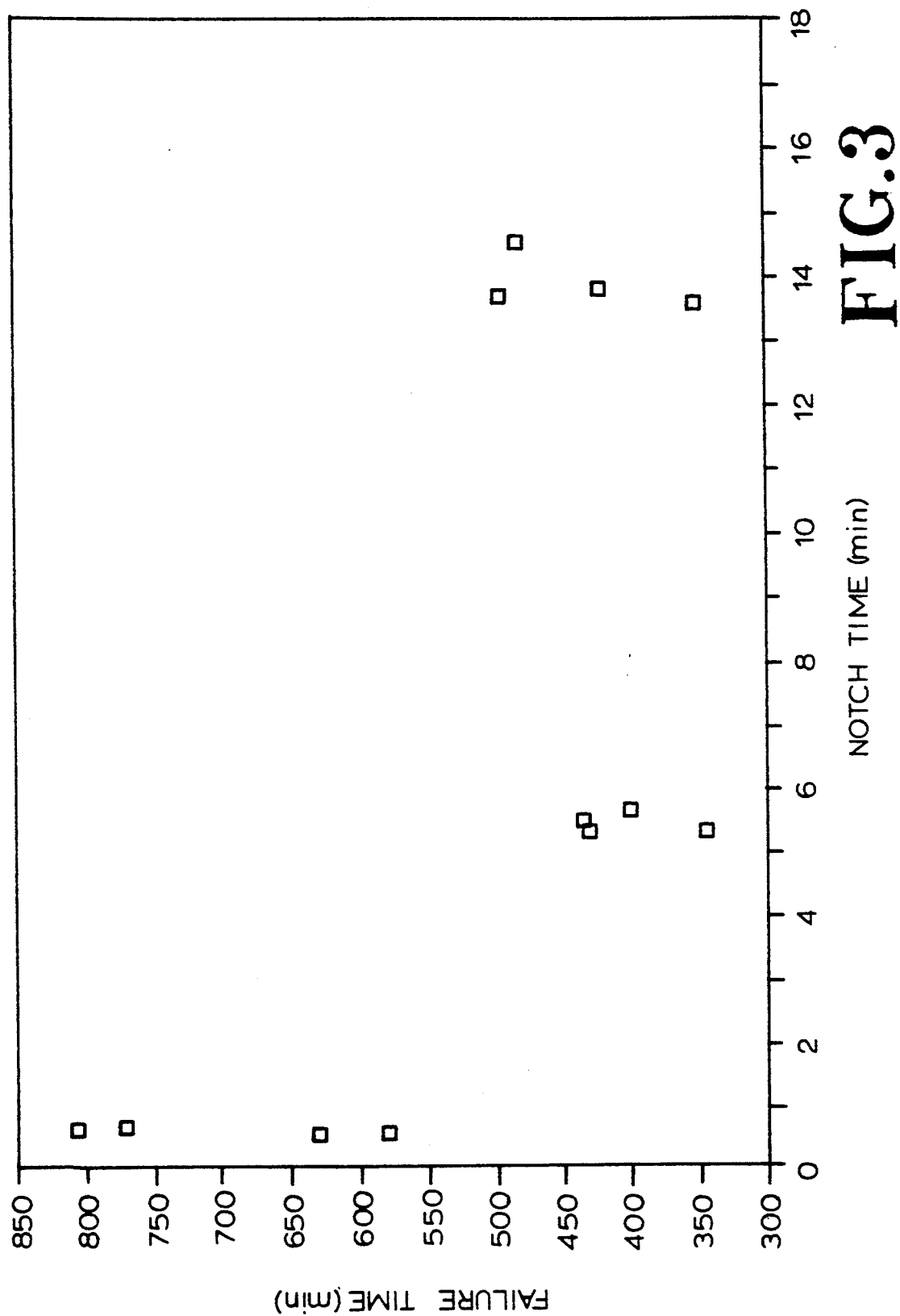
FIG. 3: is a graph depicting failure time (minutes) versus notching time (minutes) for specimens notched with the notching device of this invention.

This trend demonstrates a transition, from the failure times under standard conditions to the longer times, which occurred between about the one minute and five minute notching times for 3.5 mm notches, as depicted in FIG. 3.

The failure process of the samples tested is a common one for the slow crack growth failure in polyethylene. The notch is introduced, and as the sample is initially loaded, fibrils form at the tip of the notch area. These fibrils are the initial restraining force for the crack growth. As these fibrils give way, the sample continues to pull apart, breaking successive fibrils. The rapid increase in crack opening occurs after sufficient initial fibrils fail and thus only a relatively small area of sample is resisting the crack growth. The time for this process can not be decreased by any means, short of changing the standard conditions. Thus the standard failure mode dictates a rugged set of conditions that are standard for the industry and will only be changed if faster, more accurate results can be obtained in a different manner.

Figure 4:
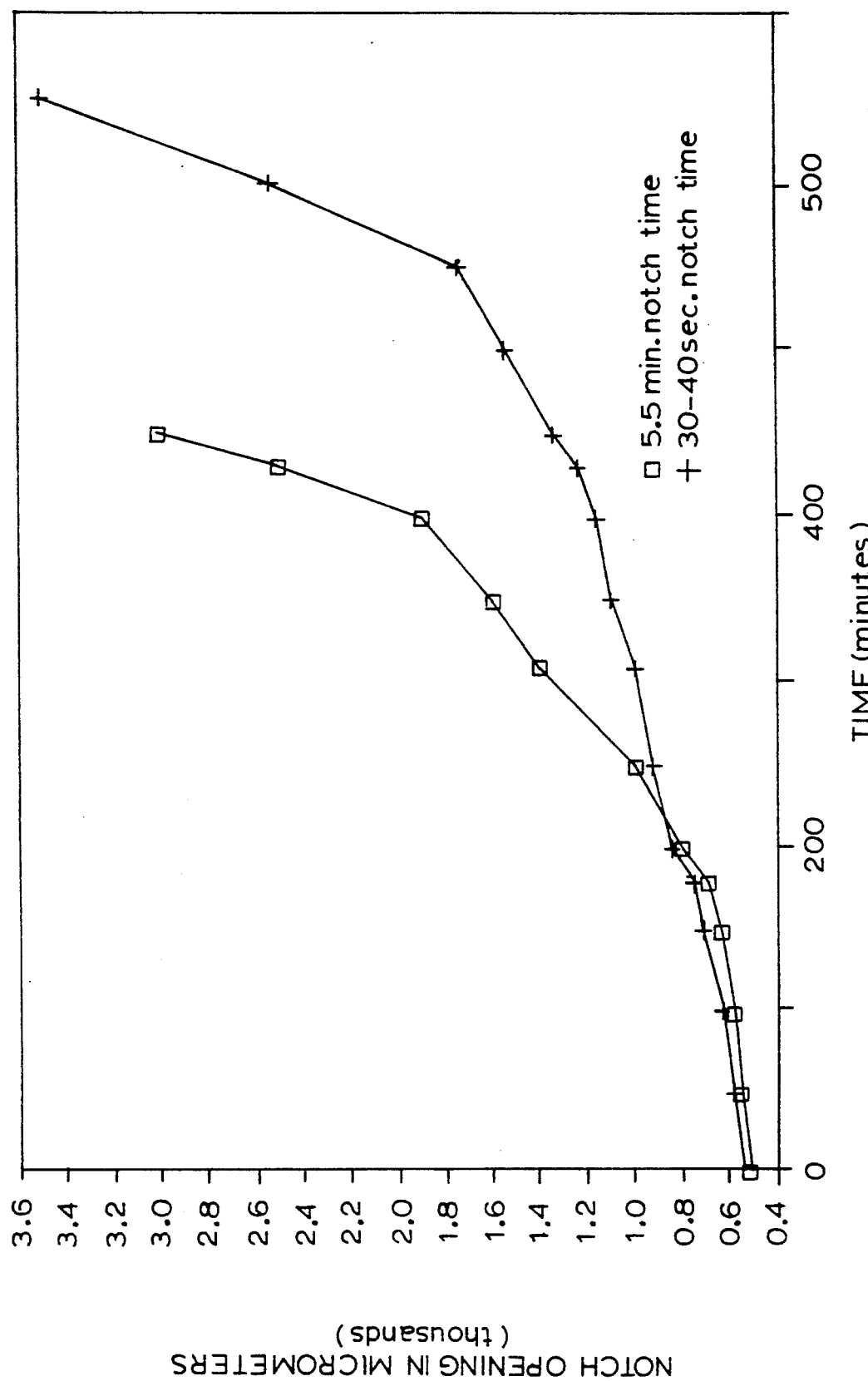
FIG. 4: is a graph depicting notch opening (μm) versus loading time (minutes) for polymeric specimens notched with the notching device of this invention.

In an effort to analyze the slow crack growth failure for the polyethylene, a measure of the crack opening was performed during several failure tests and a representative pair of curves were plotted in FIG. 4. A test temperature of 80° C., load stress of 2.4 MPa, and notch depth of about 3.5 mm was employed for the data in both curves of FIG. 4. For a typical sample notched in five and one-half minutes, the initial opening width is approximately 500 μm. The opening then widens with time with an average rate of 0.76 μm/min. This continues until approximately 200 minutes whereupon the rate increases to about 5.2 μm/min. Finally, the sample fails, after a brief crack growth rate of about 25 μm/min., as shown in FIG. 4. The final crack width just prior to failure is approximately 4500 μm.

In contrast, a fast-notched (30–40 seconds) sample behaves differently. Similar to the five minute samples, the initial crack opening averages around 500 μm. In addition, the initial rate of crack growth for fast-notched samples is approximately 0.80 μm/min. This low rate, however continues until 450 minutes, whereupon the rate increases to 4–5 μm/min. and finally to 25 μm/min., after which it fails. Thus the length of time of the initial, slowest crack growth is significantly greater for a fast notched sample. Again, similar to the five-minute-notch samples, the crack width just prior to failure is approximately 4500 μm.

What is revealing about this data is the fact that the crack growth for both samples followed a common path. That is, although the samples notched at a faster time took longer to fail, the lower portion of the crack growth closely followed that of the samples notched more slowly. Up to about 225 minutes, the samples behaved almost identically. Only after about 225 minutes, did samples notched at a slower speed rapidly increase in crack width and fail, while samples notched in about 40 seconds continued with approximately the same slope until about 450 minutes, when they too experienced an increase in crack width at a faster rate and eventually failed. Therefore, the increase in failure time would seem to center around the effects on the fast-notched sample between 200 and 400 minutes. (See Area A, FIG. 4). It is clear that this difference in failure times is caused by increased deformation due to the faster notching speed.

The slow-notched samples overcome the initial fibrils and the rate of slow-crack growth continues to increase after 225 minutes. The fast-notched samples, however, overcome the initial fibrils and then strike another obstacle, the increased deformation area produced by the fast moving razor.

As the razor is pushed into the sample, the polymer immediately ahead of the tip of the razor is deformed. The faster the razor moves, the greater extent of damage is done to the sample. This damage located "ahead" of the notch at some depth, i.e., in the specimen matrix beyond the leading edge portion of the notch, is similar to that shown in Lu et al. FIG. 9(b)–(d), and is directly responsible for the extended slow-crack growth of examples notched at fast speeds or with sliding razors or rotary cutters. The specimens prepared in accordance with this invention include notches not having any such significant residual stresses forming "ahead" of the notch, and only have a damage zone "immediately adjacent" to, and preferably contiguous with, the leading edge portion or end region of said notch, such as the 20–25 μm "arrow"-shaped damage zone shown in Lu et al. FIG. 10.

The deformation which forms ahead of the notch by prior art notching techniques slows the crack down by effectively "pinching" the crack tip. Although this deformation area is being pulled apart by the load, it is simultaneously contracting at the tip of the crack in order to compensate for the plane strain it is experiencing. Thus, the increased deformation area present in the fast-notched samples causes the rate of slow crack growth to remain essentially constant, until the crack has penetrated far enough into the sample so that the reduced area under strain is the overwhelming factor in crack growth. For the fast-notched sample this occurs only after approximately 425 minutes.

This effect can be overcome if the razor is slowed at the appropriate time or notch depth. The area of deformation is created at the end of the notch process, and if the razor is slowed sufficiently before it reaches the 3.5 mm mark, for example, prior to about the 2.5 mm mark, then extensive deformation ahead of the notch, can be avoided.

As an experiment to save time and resources, five samples were notched with the same razor. The samples were all notched with a speed of 640 μm/min. The samples were then loaded and tested under otherwise standard conditions. The five failure times for the successively notched samples were 417.4, 472.8, 406.8, 453.2 and 390.3 minutes respectively. Thus, an initial indication would be that there is negligble effect on failure time caused by using an "old" blade, at least up to about five samples.

From the foregoing, it can be realized that this invention provides methods for notching polymeric and other specimens which produces reproducible crack propagation data while minimizing testing time to a negligible amount. This invention also provides a relatively inexpensive and efficient apparatus for creating notches in specimens subject to later slow crack growth failure tests. Although various embodiments have been illustrated, this was for the purpose of describing and not limiting the invention. Various modifications, which will become apparent to one skilled in art, are within the scope of this invention as set forth in the attached claims.

What is claimed is:

1. A notching machine for preparing a notch in a mechanical testing specimen, comprising:
   (a) razor means for creating said notch in said specimen;
   (b) specimen holder means for restraining said specimen during the preparation of said notch; and
   (c) motorized mechanical actuation means for forming said notch without any significant residual stresses forming ahead of said notch by substantially linearly contacting said razor means with said specimen in a direction which is substantially normal to the surface of said specimen receiving said notch, said notch forming occurring at a rate of about 350 μm/min. to about 3500 μm/min., at least when forming an end region of said notch.

2. The notching machine of claim 1, wherein said actuation occurs at a rate of about 700–1000 μm/min. at least when forming an end region of said notch.

3. The notching machine of claim 1, wherein said razor means comprises a single-edge razor blade.

4. The notching machine of claim 4, wherein said specimen contains a damage zone immediately adjacent to a leading edge portion of said notch.

5. The notching machine of claim 4, wherein said motorized mechanical actuation means provides said actuation at a constant rate.

6. The notching machine of claim 1 further comprising a specimen holder for restraining said specimen during said actuation of said razor means.

7. The notching machine of claim 1 further comprising retraction means for selectively disengaging said razor means from said specimen after said notch is prepared.

8. The notching machine of claim 1 further comprising gauge means for determining a dimension of said notch during said actuation.

9. A notching machine for preparing a notch in a polymeric specimen for slow crack failure testing, comprising:
  (a) razor means for creating said notch in said polymeric specimen;
  (b) specimen holder means for restraining said specimen during the preparation of said notch; and
  (c) motorized mechanical actuation means for substantially linearly actuating said razor means into said specimen in a direction which is substantially normal to a stress created in said polymeric specimen during said testing, said actuation occurring at a rate of about 350 μm/min. to about 3500 μm/min., at least when forming an end region of said notch.

10. The notching machine of claim 9, wherein said actuation occurs at a rate of about 700–1000 μm/min. at least when forming an end region of said notch.

11. The notching machine of claim 9, wherein said razor means comprises a single-edge razor blade.

12. The notching machine of claim 11 further comprising motor means for providing constant rate actuation of said razor means.

13. The notching machine of claim 9, wherein said notch has a depth of less than about 3.5 mm.

14. The notching machine of claim 13, wherein said notch is selected to be contiguous with side notches of about 1 mm in depth to ensure substantially 100% plane strain.

15. A method of preparing a notch in a mechanical testing specimen, comprising forming said notch without any residual stresses forming ahead of said notch by linearly actuating a razor means into said testing specimen in a direction which is substantially normal to the surface of said specimen receiving said notch, said actuating occurring at a rate of about 350 μm/min. to about 3500 μm/min., at least when forming an end region of said notch.

16. The method of claim 15, wherein said actuation occurs at a rate of about 700–1000 μm/min. at lest when forming an end region of said notch.

17. The method of claim 15, wherein said razor means comprises a single edge razor blade.

18. The method of claim 17, wherein said mechanical testing specimen comprises a polymer.

19. A method of slow-crack failure testing of a notched polymeric testing specimen wherein said notch is prepared in accordance with the method of claim 15.

20. The method of slow-crack failure testing of claim 19, wherein said specimen comprises polyethylene and said testing occurs at a temperature of less than about 80° C.

21. The method of slow-crack failure testing of claim 20, wherein said notch is propagated under a load of at least about 2.4 MPa/cm$^2$.

* * * * *